(12) United States Patent
Kobayashi et al.

(10) Patent No.: US 6,699,029 B2
(45) Date of Patent: *Mar. 2, 2004

(54) OXYGEN ENHANCED SWITCHING TO COMBUSTION OF LOWER RANK FUELS

(75) Inventors: Hisashi Kobayashi, Putnam Valley, NY (US); Lawrence E. Bool, III, East Aurora, NY (US); Kuang Tsai Wu, Williamsville, NY (US)

(73) Assignee: Praxair Technology, Inc., Danbury, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/194,574

(22) Filed: Jul. 11, 2002

(65) Prior Publication Data

US 2003/0099913 A1 May 29, 2003

Related U.S. Application Data

(63) Continuation-in-part of application No. 09/757,611, filed on Jan. 11, 2001, now abandoned.
(60) Provisional application No. 60/380,817, filed on May 15, 2002, and provisional application No. 60/380,818, filed on May 15, 2002.

(30) Foreign Application Priority Data

Dec. 20, 2001 (WO) .............................. PCT/US01/48713

(51) Int. Cl.$^7$ .......................... F23M 3/04; F23M 3/02; F23J 11/00
(52) U.S. Cl. .............................. 431/10; 431/8; 110/345
(58) Field of Search .......................... 431/10, 8, 351; 110/344, 345, 348

(56) References Cited

U.S. PATENT DOCUMENTS 3,656,878 A 4/1972 Wright (List continued on next page.)

FOREIGN PATENT DOCUMENTS

| DE | 4142401 | 6/1993 |
| EP | 0653590 | 11/1984 |
| EP | 0187441 | 7/1986 |

OTHER PUBLICATIONS

Michelfelder, S. et al., "Transfer de chaleur et pollution", Revue Generale De Thermique, No. 196 (Apr. 1978), p. 324 (with translation).

Sarofim, A.F. et al., "Strategies For Controlling Nitrogen Oxide Emissions During Combustion Of Nitrogen–Bearing Fuels", The American Institute of Chemical Engineers, (1978), No. 175, vol. 74, pp. 67–92.

(List continued on next page.)

*Primary Examiner*—Alfred Basichas
(74) *Attorney, Agent, or Firm*—Donald T. Black

(57) ABSTRACT

A furnace that combusts fuel, such as coal, of a given minimum energy content to obtain a stated minimum amount of energy per unit of time is enabled to combust fuel having a lower energy content, while still obtaining at least the stated minimum energy generation rate, by replacing a small amount of the combustion air fed to the furnace by oxygen. The replacement of oxygen for combustion air also provides reduction in the generation of NOx.

7 Claims, 2 Drawing Sheets

U.S. PATENT DOCUMENTS

| | | |
|---|---|---|
| 3,873,671 A | 3/1975 | Reed et al. |
| 4,329,932 A | 5/1982 | Takahashi et al. |
| 4,343,606 A | 8/1982 | Blair et al. |
| 4,388,062 A | 6/1983 | Bartok et al. |
| 4,408,982 A | 10/1983 | Kobayashi et al. |
| 4,427,362 A | 1/1984 | Dykema |
| 4,488,866 A | 12/1984 | Schirmer et al. |
| 4,495,874 A | 1/1985 | Greskovich et al. |
| 4,515,095 A | 5/1985 | Greskovich |
| 4,541,796 A | 9/1985 | Anderson |
| 4,556,384 A | 12/1985 | Laurenceau et al. |
| 4,596,198 A | 6/1986 | Greskovich et al. |
| 4,761,132 A | 8/1988 | Khinkis |
| 4,797,087 A | 1/1989 | Gitman |
| 4,863,371 A | 9/1989 | Ho |
| 4,878,830 A | 11/1989 | Henderson |
| 4,899,670 A | 2/1990 | Hansel |
| 4,946,382 A | 8/1990 | Kobayashi et al. |
| 4,957,050 A | 9/1990 | Ho |
| 4,969,814 A | 11/1990 | Ho et al. |
| 4,973,346 A | 11/1990 | Kobayashi |
| 4,988,285 A | 1/1991 | Delano |
| 5,000,102 A | 3/1991 | Ho |
| 5,076,779 A | 12/1991 | Kobayashi |
| 5,085,156 A | 2/1992 | Dykema |
| 5,158,445 A | 10/1992 | Khinkis |
| 5,186,617 A | 2/1993 | Ho |
| 5,195,450 A | 3/1993 | Marion |
| 5,201,650 A | 4/1993 | Johnson |
| 5,203,859 A | 4/1993 | Khinkis et al. |
| 5,213,492 A | 5/1993 | Ho |
| 5,242,296 A | 9/1993 | Tuson et al. |
| 5,291,841 A * | 3/1994 | Dykema .................. 110/347 |
| 5,308,239 A | 5/1994 | Bazarian et al. |
| 5,387,100 A | 2/1995 | Kobayashi |
| 5,411,394 A | 5/1995 | Beer et al. |
| 5,413,476 A | 5/1995 | Baukal, Jr. et al. |
| 5,439,373 A | 8/1995 | Anderson et al. |
| 5,454,712 A | 10/1995 | Yap |
| 5,601,425 A | 2/1997 | Kobayashi et al. |
| 5,609,662 A | 3/1997 | Kobayashi et al. |
| 5,611,682 A | 3/1997 | Slavejkov et al. |
| 5,611,683 A | 3/1997 | Baukal, Jr. et al. |
| 5,725,366 A | 3/1998 | Khinkis et al. |
| 5,832,847 A | 11/1998 | Liesse et al. |
| 5,871,343 A | 2/1999 | Baukal et al. |
| 5,904,475 A | 5/1999 | Ding |
| 5,924,858 A | 7/1999 | Tuson et al. |
| 5,931,654 A | 8/1999 | Chamberland |
| 6,007,326 A | 12/1999 | Ryan, III et al. |
| 6,030,204 A * | 2/2000 | Breen et al. .................. 431/4 |
| 6,085,674 A | 7/2000 | Ashworth |
| 6,113,389 A | 9/2000 | Joshi et al. |
| 6,171,100 B1 | 1/2001 | Joshi et al. |
| 6,206,949 B1 | 3/2001 | Kobayashi et al. |
| 6,244,200 B1 | 6/2001 | Rabovitser et al. |
| 6,276,928 B1 | 8/2001 | Joshi et al. |
| 6,289,851 B1 | 9/2001 | Rabovitser et al. |
| 6,314,896 B1 | 11/2001 | Marin et al. |
| 6,325,003 B1 * | 12/2001 | Ashworth et al. .......... 110/345 |
| 6,357,367 B1 * | 3/2002 | Breen et al. ................ 110/345 |
| 6,394,790 B1 | 5/2002 | Kobayashi |
| 6,398,546 B1 | 6/2002 | Kobayashi |
| 6,409,499 B1 | 6/2002 | Feldermann |
| 6,418,865 B2 | 7/2002 | Marin et al. |
| 6,519,973 B1 | 2/2003 | Hoke, Jr. et al. |

OTHER PUBLICATIONS

Timothy, L.D. et al., "Characteristics Of Single Particle Coal Combustion", $19^{th}$ Symposium on Combustion, The Combustion Institute (1982), pp. 1123–1130.

Farmayan, W.F. et al., "$NO_x$ and Carbon Emission Control in Coal– Water Slurry Combustion", Sixth International Symposium on Coal Slurry Combustion and Technology, Orlando, FL, (1984).

"Oxygen Enriched Air/Natural Gas Burner System Development", Final Report, Gas Research Institute (1989), pp. 140 and 186–189.

Kobayashi, H. et al., "$NO_x$ Emission Characteristics of Industrial Burners and Control Methods Under Oxygen Enriched Combustion Conditions", International Flame Research Foundation, $9^{th}$ Members Conference, Noordwijkerhout (1989).

Baukal, C.E. et al., "$NO_x$ Measurements In Oxygen–Enriched, Air–Natural Gas Combustion Systems", Fossil Fuel Combustion Symposium, (Amer. Soc. Mech. Eng., 1990), pp. 75–79.

Baukal, C.E. et al., "Oxygen Enrichment Enhances Combustion", Air Products and Chemicals, Inc., (before 1992), pp. 17–23.

Panahi, S.K. et al., "Low–$NO_x$ Technologies For Natural Gas–Fired Regenerative Glass Melters", presented at Scandinavian Society of Glass Technology, Institute of Gas Technology (1992), pp. 1–15.

"Catalog of Technical Reports", Gas Research Institute, (Dec. 1992).

Eddings, E.G. et al. "Advances in the Use of Computer Simulations for Evaluating Combustion Alternatives", presented at the $3^{rd}$ CREST International Symposium on High Temperature Air Combustion and Gasification, Yokohama, Japan (Mar. 2000).

Takano, S. et al. "$CO_2$ Recovery from PCF Power Plant with $O_2/CO_2$ Combustion Process", IHI Engineering Review, Oct. 1995, pp. 161–164.

Campbell, D.A. et al. "Oxy–coal injection at Cleveland Ironworks", Ironmaking and Steelmaking, 1992, vol. 19 No. 2, pp. 120–125.

Riley, M.F. "Effect of Direct Oxygen Injection on Combustion of Injected Coal", Proc. $2^{nd}$ Internat. Cong. on the Sci. and Tech. of Ironmaking, ISS, 1998, pp. 683–688.

Book, L., "Oxygen Enhanced Combustion of Biomass and Biosolids", 2001 Joint AFRC/JFRC/IEA Int'l Combustion Symposium, Kauai, Hawaii (Sep. 9–12, 2001).

* cited by examiner

OXYGEN ENHANCED SWITCHING TO COMBUSTION OF LOWER RANK FUELS

This application is a continuation-in-part of application Ser. No. 09/757,611 filed Jan. 11, 2001 now abandoned, and claims priority from U.S. Provisional Application Serial No. 60/380,817 filed May 15, 2002 and U.S. Provisional Application Serial No. 60/380,818 filed May 15, 2002. The entire contents of said three applications are hereby incorporated herein by reference.

This invention was made with United States Government support under Cooperative Agreement No. DE-FC26-00NT40756 awarded by the Department of Energy. The United States Government has certain rights in the invention.

FIELD OF THE INVENTION

The present invention relates to combustion of carbonaceous and hydrocarbonaceous fuels, such as coal.

BACKGROUND OF THE INVENTION

One of the methods to reduce NOx and other emissions from coal fired utility boilers is to switch to a less polluting coal, e.g., from an Eastern bituminous coal to a Western sub-bituminous coal. (According to ASTM D 388, classification of coals by rank, the fixed carbon content and the calorific values are used as the basic criteria for classification of coals. Lignite is defined as having calorific values less than 8,300 Btu/lb on a moist and mineral matter free basis. Sub-bituminous coals are defined as having calorific values between 8,300 and 11,500 Btu/lb. High volatile bituminous coals are defined as having calorific values between 11,500 and 14,000 Btu/lb. These definitions apply when the foregoing terms are used herein. Medium and low volatile bituminous coals and anthracites are classified based on their fixed carbon contents.)

Western sub-bituminous coals and lignites typically have much lower sulfur contents and lower nitrogen contents than Eastern bituminous coals. Furthermore, sub-bituminous coals and lignites are more reactive than bituminous coals and produce lower unburned carbon (UBC) in ash. Emissions of SOx and NOx and UBC in ash can be substantially reduced by switching to less polluting coals.

There are, however, several technical issues in switching to a lower rank coal as all or even a portion of the fuel fed to a boiler designed for firing bituminous coals. For example, the existing coal pulverizer designed for a bituminous coal may not be able to handle the greater volume of sub-bituminous coal to provide the same heat input to the boiler. Also, the heating value of a sub-bituminous coal or lignite is much lower and the moisture content is higher than those of a bituminous coal. As a result, the flame temperature is reduced and a larger flue gas volume is produced per unit amount of heat released. The lower flame temperature and higher flue gas volume associated with a subbituminous coal typically cause a problem in heat absorption and distribution: reduced heat absorption in the radiant section and too much heat passing through the radiant section and being absorbed in the convective section. This sometimes results in a derating of the boiler, unless major modifications are made to the boiler.

To overcome capacity limitations of the existing coal pulverizer designed for a bituminous coal design modifications that increase air flow, duct heaters and mechanical capacity upgrades may be required. In-duct heaters are used to reduce the moisture content of pulverized coal so as to improve the flame ignition characteristics and to increase the flame temperature with lower rank coals. A careful analysis of boiler heat transfer conditions is required to assess the impact of reduced heat transfer to the plant steam and power outputs. Modification of the steam circuits may be required to properly balance the radiative and convective sections of the boiler. For example, economizer tubes may be added for additional heat recovery from flue gas. Furthermore, the spacing of the superheat and reheat sections and gas temperature need to be reviewed for potential fouling and plugging issues. Additional soot blower coverage or water cleaning devices for the furnace walls may need to be used. (Robert Lewis, Gary Camody, and Patrick Jennings, "Summary of Recent Low NOx achievements with Low NOx Firing Systems and High Reactivity PRB and Lignite Coal: As low as 0.1 Lb/MMBtu," also James Topper, et al, "Maximizing PRB Coal Usage in Conjunction with In-Furnace NOx Solutions to Minimize Cost of NOx Compliance," both papers presented at $27^{th}$ International Conference on Coal Utilization & Fuel Systems, Mar. 4–7, 2002, Clearwater, Fla.).

Although these boiler modifications have been successfully implemented to enable coal switching from bituminous coal to sub-bituminous coal, significant capital and opportunity costs are typically incurred due to the equipment and labor costs of the modification and due to the boiler down time while the modifications are being made. There is accordingly a need to provide a method to obtain the reduced NOx emissions from an existing coal fired boiler that can be realized by switching the type of coal in the fuel, without requiring major modifications to the existing boiler. A further object of the present invention is to enhance the reduction of NOx emissions by improved combustion modifications.

BRIEF SUMMARY OF THE INVENTION

The present invention is a method for modifying operation of a furnace, comprising to a furnace that comprises a combustion chamber, burner means for combusting hydrocarbonaceous fuel containing bound nitrogen and having a given minimum calorific value in said combustion chamber to generate heat of combustion and gaseous combustion products, feed means for feeding said fuel and combustion air to said burner means, flue means for enabling said combustion products to leave said combustion chamber, and heating means for using said heat of combustion to produce steam, wherein said furnace is being operated to combust a first fuel containing bound nitrogen and having said minimum calorific value to produce steam at a defined minimum rate of energy content per unit of time, providing replacement fuel by replacing some or all of said first fuel with a second hydrocarbonaceous fuel whose calorific value is below that of the first fuel, at a replacement ratio such that the feed rate of said second fuel to said furnace divided by the feed rate of said first fuel to said furnace in units of energy per unit time is between 1.0 to 1.3, and feeding said replacement fuel to said burner means, feeding gaseous oxygen into said replacement fuel as the replacement fuel emerges from said burner into said combustion chamber or by adding it to the air fed through said burner, in an amount which is less than 25% of the stoichiometric amount required for complete combustion of said replacement fuel while reducing the amount of air fed through said burner by an amount containing sufficient oxygen that the overall stoichiometric ratio in said furnace varies by not more than 10% compared to the stoichiometric ratio without said addition of oxygen, and combusting said replacement fuel with said combustion air and said oxygen,.

In a preferred embodiment, the calorific values of said first fuel and said second fuel are related such that the available heat above 2000 F. generated by combusting said first fuel with air at a given stoichiometric ratio and temperature is 103% or more of the available heat above 2000 F. generated by combusting said second fuel with air at said given stoichiometric ratio and temperature.

In another preferred embodiment, said oxygen is fed to said burner at a sufficient rate that said furnace produces steam at a rate of energy content per unit of time at least equal to said defined minimum rate.

In yet another preferred embodiment, said first fuel is bituminous coal and said second fuel optionally comprises bituminous coal and further comprises coal selected from the group consisting of subbituminous coal, lignite and mixtures thereof.

In preferred embodiments of the combustion, said combustion is staged with over fire air and the primary combustion zone stoichiometric ratio is between 0.6 and 1.0.

In a preferred embodiment of operation, a stream of fuel is fed through said burner and oxygen is fed into said fuel by injecting it through a hollow lance, positioned in said stream, into the fuel as the fuel emerges from the burner. In another preferred embodiment of operation, a stream of fuel is fed through an annular fuel passage of said burner, and oxygen is fed into said fuel by injecting it through an annular passage surrounding or surrounded by said annular fuel passage.

In the present invention a small amount of oxygen is used in conjunction with switching at least some, or all, of the fuel to a lower rank (lower energy content per unit mass) fuel to reduce pollution emissions, in a manner which eliminates the needs for costly boiler modifications. A preferred embodiment is to switch some or all of the feed from bituminous coal to sub-bituminous coal or lignite. For ease of reference, the term "replacement fuel" is sometimes used herein, to refer to the fuel that is fed to the combustion chamber. When a portion of the combustion air is replaced by oxygen the flame temperature is increased and the flue gas volume is reduced because the reduced flow rate of air reduces the amount of nitrogen flowing through the combustion chamber. The oxygen addition effectively offsets the reduction in flame temperature and increased flue gas volume caused by switching the feed coal to a lower rank coal and restores the heat transfer conditions in the boiler. Furthermore, oxygen addition can be conducted under staged combustion conditions so as to enhance NOx reduction kinetics in the fuel rich combustion stage, as described herein.

As used herein, "stoichiometric ratio" means the ratio of oxygen fed, to the total amount of oxygen that would be necessary to convert fully all carbon, sulfur and hydrogen present in the substances comprising the feed to carbon dioxide, sulfur dioxide, and water.

As used herein, "NOx" means oxides of nitrogen such as but not limited to NO, $NO_2$, $NO_3$, $N_2O$, $N_2O_3$, $N_2O_4$, $N_3O_4$, and mixtures thereof.

As used herein, "SOx" means oxides of sulfur such as but not limited to $SO_2$, $SO_3$, and mixtures thereof.

As used herein, "bound nitrogen" means nitrogen that is part of a molecule that also contains carbon and hydrogen and optionally also oxygen.

As used herein, "staged combustion with low NOx burners" means combustion in a furnace wherein mixing with fuel of a portion of the combustion air required for complete combustion of the fuel is delayed to produce a flame with a relatively large fuel rich flame zone As used herein, "globally staged combustion or staged combustion with over fire air" means combustion in a furnace wherein a portion of the combustion air (the "over fire air") required for complete combustion of the fuel is fed to the furnace not through or immediately adjacent any burner but instead through one or more inlets situated between the burner(s) and the furnace flue means, and is fed without an associated feed of fuel.

DETAILED DESCRIPTION OF THE INVENTION

DETAILED DESCRIPTION OF THE INVENTION

The invention will be described with reference to the Figures, although a description that refers to the Figures is not intended to limit the scope of that which is considered to be the present invention.

Figure 1:
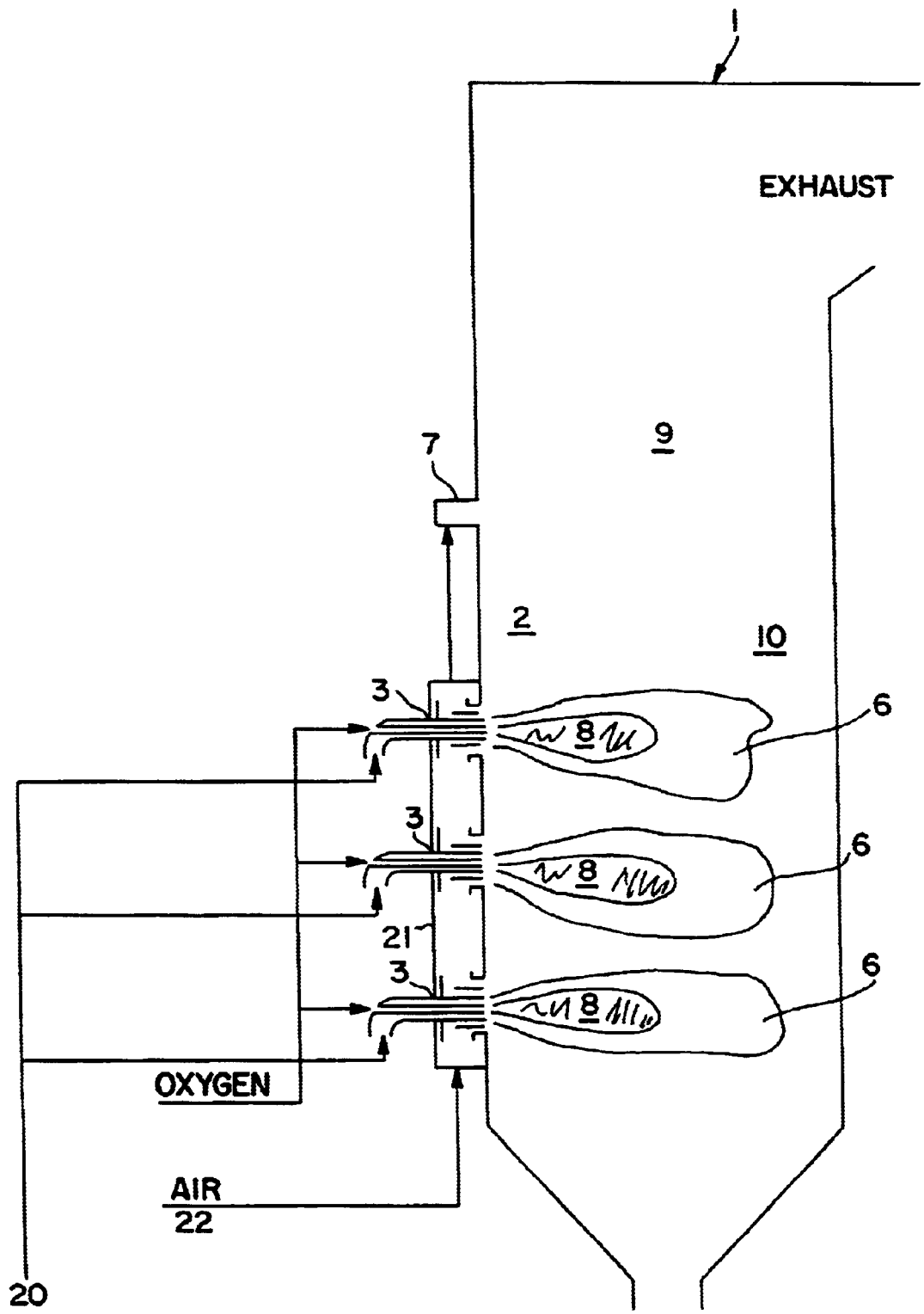
FIG. 1 is a cross-sectional representation of one embodiment of apparatus for carrying out the present invention.

FIG. 1 shows combustion device 1, which can be any apparatus wherein combustion is carried out in the interior 2 of the device. Preferred combustion devices include furnaces and boilers which are used to generate electric power by conventional means, not shown.

Each burner 3 in a sidewall or end wall of combustion device 1 feeds fuel, air and oxygen from sources thereof outside the combustion device 1 into the interior 2 of combustion device 1. Suitable fuels include hydrocarbon liquids, such as fuel oil, and also include pulverulent hydrocarbon solids, a preferred example of which is pulverized coal or petroleum coke.

Figure 2:
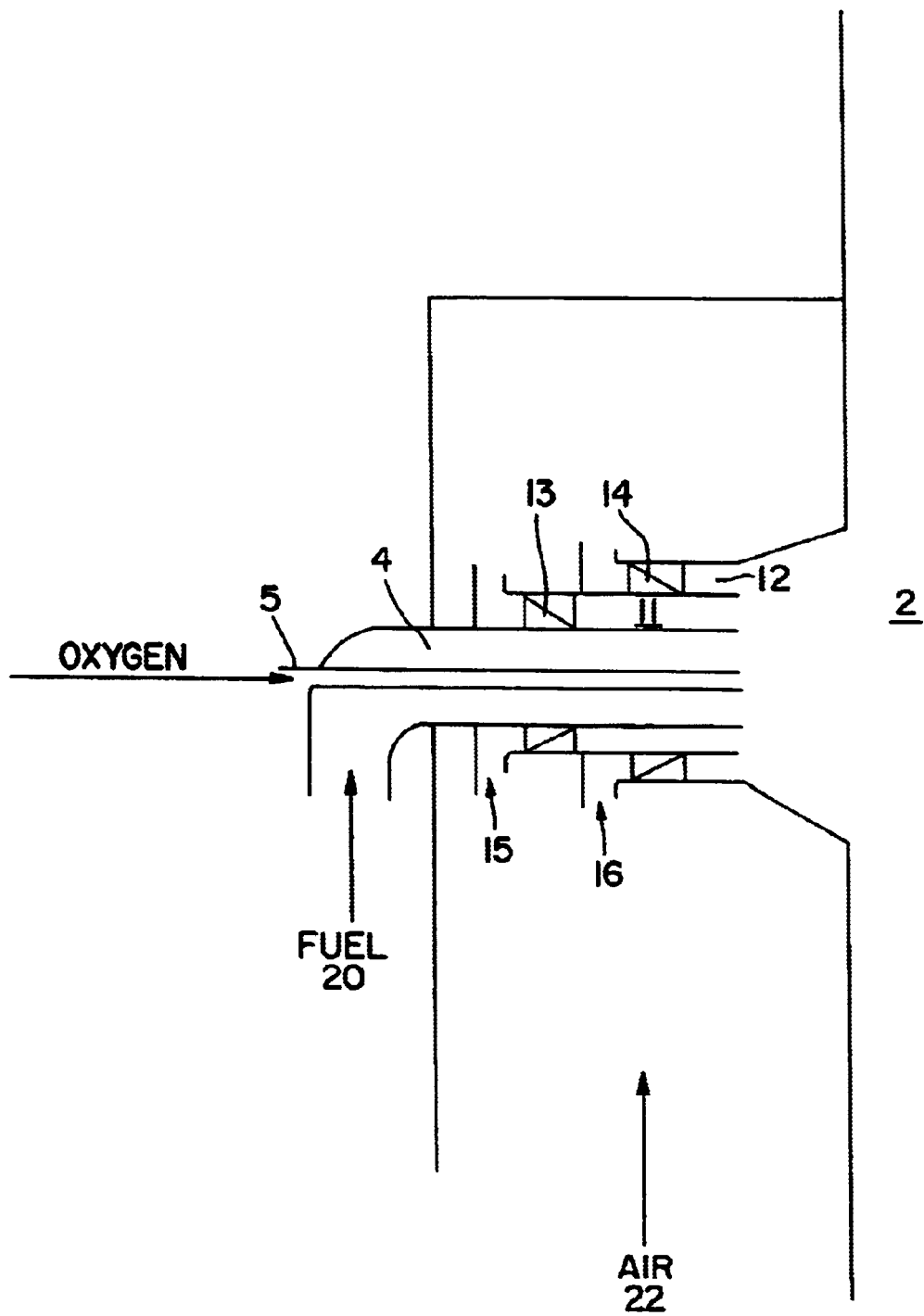
FIG. 2 is a cross-sectional representation of a burner useful for carrying out the present invention.

As seen in FIG. 1 and more closely in FIG. 2, burner 3 is preferably comprised of several concentrically arranged passages, although other constructions to the same effect can be used. The fuel is fed into combustion device 1 through annular passage 4, disposed concentrically around lance 5 through which oxygen is fed as described herein. Preferably, the fuel is transported from a supply source 20 to one or more burners 3 and propelled through burner 3 into the interior 2 of combustion device 1, by suitable pump means in the case of liquids such as fuel oil, and by blowers and impellers of conventional design in the case of hydrocarbon solids such as pulverized coal, which are conventionally fed into the combustion device with the aid of transport air or primary air. Liquid hydrocarbon fuels are preferably fed through one or more atomizing nozzles of conventional design, to feed the liquid fuel into the combustion chamber as discrete, dispersed droplets with atomizing air. An effective amount typically about 1.5 to 2.0 lb of primary air is used to transport 1 lb of coal, which corresponds to about 20% of the stoichiometric combustion air required for complete combustion of bituminous coal. For combustion of heavy oil about 0.5 to 1.0 lb of primary air is typically used to atomize 1 lb of oil.

Combustion air 22 is supplied by a forced draft ("FD") fan to one or more windboxes 21 and fed to air passages of one or more burners 3. Secondary combustion air 15 is fed through burner 3 into combustion device 1, preferably through concentrically arranged annular passages 11 surrounding the annular space 4 through which the hydrocarbon fuel is fed. Preferably tertiary combustion air 16 is fed through burner 3 into combustion device 1, preferably through concentrically arranged annular passages 12 surrounding the secondary air passage. Preferably combustion air is also fed through over fire air port 7 (seen in FIG. 1) into combustion device 1. Preferably, the oxygen is fed into the interior 2 of the device apart from the secondary and tertiary combustion air. That is, the oxygen that is fed through burner 3 in accordance with this invention is preferably not commingled with the secondary and tertiary combustion air before or after it is fed into combustion device 1, especially when no over fire air is used.

Preferred low NOx burners have primary (fuel), secondary and tertiary air passages for good aerodynamic adjustability. However, other low NOx burner designs using only primary and secondary air feeds can be used. Once the optimum settings with the three passages have been determined, the secondary air swirl vanes and passage can be designed to create about the same aerodynamic mixing characteristics as with the three-passage design. Alternatively, burners with an additional (quaternary) passage can be used (such as the RSFC™ burner described in U.S. Pat. No. 5,960,724).

Before a combustion device is retrofitted in accordance with the present invention to reduce the formation of NOx formed in the operation of the combustion device, lance 5 for feeding oxygen is not yet present. Combustion is carried out between the hydrocarbon fuel and the oxygen in the combustion air, resulting in formation of a flame 6. The region 8 of the flame closest to the end of burner 3, that is, where the hydrocarbon fuel emerges from the burner, is a fuel-rich zone. The area of the flame 6 around its periphery, is relatively lean, as secondary and tertiary combustion air has not been fully reacted with fuel. When a sufficient amount of air is fed from over fire air port 7 for global combustion staging, the entire lower zone of the furnace, or primary combustion zone (PCZ) 10, below over fire air port 7 becomes fuel rich, except the areas near burners 3 where air is injected and not yet fully reacted with fuel.

Then, lance 5 is added. Alternatively, a burner that feeds fuel and combustion air is replaced with a burner that performs as shown in the Figures and described herein.

Preferably, air is also fed through over fire air port opening 7 into the interior of combustion device 1, to make the primary combustion zone 10 more fuel rich and to provide additional oxygen helping to achieve complete combustion of the fuel in the burnout zone 9. The oxygen in the combustion air fed through burner 3, combined with the oxygen fed at opening 7, are sufficient to enable complete combustion of the fuel, and typically contain 10 to 15 volume percent excess oxygen over the amount required for the complete combustion of the fuel.

Preferably, the secondary and tertiary combustion air are fed at the burner 3 so as to swirl about a longitudinal axis, thereby creating a recirculation zone near each burner and improving commingling of air and fuel. Swirl can be achieved by known techniques, such as providing deflectors, 13 and 14, in the annular passages for secondary and tertiary air flow of the burner which direct the flow of the streams in the desired swirling direction. It is preferred to provide a high degree of swirl, preferably a swirl number, as defined in "Combustion Aerodynamics", J. M. Beer and N. A. Chigier, Robert E. Krieger Publishing Company, Inc., 1983, of 0.6 to 2.0.

Preferably the total amount of air fed through burner 3, i.e., the sum of primary, secondary and tertiary air, is between 60 and 95% of the stoichiometric air requirement for complete combustion. Most preferably the total amount of air fed through burner 3 is about 70 to 85% of the stoichiometric air requirement for complete combustion.

The velocity of each stream of combustion air is preferably 50 to 200 feet per second. The velocity of the oxygen injected through lance 5 is preferably within 50% to 200% of the velocity of the primary air.

Tests have suggested that a preferred approach is to expose at least some of the fuel particles or droplets to a high concentration of oxygen as opposed to uniformly enriching the overall combustion air. The simple approach of injecting oxygen into the windbox 21 of a low NOx burner such that the enriched air is fed to the entire burner, including the critical primary stage air, is not considered effective.

When oxygen is premixed or mixed rapidly into the coal transport stream using 20% of stoichiometric air and the overall combustion stoichiometric ratio is 1.15, the following average concentrations of oxygen in the transport air stream and in the overall combustion air are calculated.

| % SR air replaced with $O_2$ (*) | $O_2$ concentration in transport air (vol. %) | Avg. $O_2$ concentration in total combustion air (vol. %) |
|---|---|---|
| 0 | 21.0 | 21.0 |
| 5 | 24.9 | 21.7 |
| 10 | 28.5 | 22.5 |
| 15 | 31.7 | 23.4 |
| 20 | 34.7 | 24.3 |
| 25 | 37.4 | 25.4 |

(* e.g. 5 cf of air replaced with 1.05 cf of pure $O_2$ to give the same amount of $O_2$)

Due to the small amount of oxygen used, only modest increases in the oxygen concentration of air are achieved when mixed uniformly even when oxygen is mixed only with the transport air. A preferred method is to inject oxygen into the coal/air transport stream at the tip of the nozzle. In this case some of the coal particles are mixed with oxygen jets and locally create zones of coal high $O_2$ mixture. Such conditions may provide zones of rapid ignition sources and facilitate early ignition and devolatilization as compared to the case oxygen is premixed with the transport air stream.

Another preferred method is to inject oxygen from the inner or outer annular space adjacent to the coal stream. In this case the favorable oxygen rich combustion condition is provided at the boundary of the coal and oxygen streams.

When oxygen is injected separately at high velocity parallel to the fuel stream, as was the case for Farmayan, et al., ("NOx and Carbon Emission Control in Coal-Water Slurry Combustion", Sixth International Symposium on Coal Slurry Combustion and Technology, Orlando, Fla., Jun. 25–27, 1984), the oxygen jet(s) may be diluted quickly with surrounding gases and its effectiveness may be retarded. Thus, the method of oxygen injection has to be carefully designed.

The present invention improves, that is, lessens, the formation of NOx in the combustion device by feeding oxygen into the entering hydrocarbon fuel stream as described herein. More specifically, the oxygen (by which is meant a gaseous stream comprising at least 50 vol. % $O_2$, preferably at least 80 vol. % $O_2$, most preferably at least 90 vol. % $O_2$), is fed directly into the hydrocarbon fuel as it emerges from the burner and enters the interior 2 of combustion device 1. Thus, at least some of the particles of solid fuel, or the droplets of liquid fuel, as the case may be, enter the combustion device and the fuel-rich portion of flame 6, in a gaseous atmosphere containing a high concentration of oxygen.

When over fire air is used for global combustion staging, preferably with air burners equipped with four separate air passages, oxygen may be premixed with the primary or secondary air or both, using suitable spargers within the gas passages in burner 3.

The oxygen is preferably fed through a lance 5 or similar feed line that can be open at the end that opens into combustion device 1, or that is closed at the end and has numerous openings in its periphery adjacent that closed end, such that oxygen flows out through those openings directly into the hydrocarbon fuel entering the combustion device from the burner.

The amount of oxygen fed in this manner should be sufficient to establish a stoichiometric ratio in the fuel-rich zone of flame 6 which is less than about 0.85. The amount of oxygen fed through line 5 should be less than 25% of the stoichiometric amount required for the complete combustion of the fuel. More preferably, the amount corresponds to less than 15% of the stoichiometric amount required for complete combustion of the fuel.

At the same time, the amount of secondary and tertiary combustion air fed through burner 3 into combustion device 1, need to be decreased by an amount corresponding to the amount of oxygen fed via lance 5. More specifically, the amount of secondary and tertiary combustion, and quaternary, if used, air fed through burner 3 should be reduced by an amount containing within 10% of the amount of oxygen fed via line 5 into the fuel.

NOx emission strongly depends on the local stoichiometric conditions. As injection of oxygen makes the local stoichiometric condition leaner, one has to consider the change in the local stoichiometric conditions after the oxygen injection. For example, injection of oxygen, equivalent to 10% of the stoichiometric air, into a locally rich zone at a stoichiometric ratio of 0.4 (SR=0.4), without changing the combustion air, would alter the local stoichiometric conditions to SR=0.5 and would be expected to decrease NOx emissions substantially. Such an effect is much greater than that from "replacing 10% air with oxygen" while keeping the local stoichiometric condition constant at SR=0.4. If the same amount of oxygen is injected into the flame zone, without changing the combustion air, where the local stoichiometric condition is SR=0.95, NOx emission is expected to increase sharply if the local stoichiometric condition is increased to SR=1.05.

Thus, it is generally preferred to inject oxygen into the richest area of the flame.

Injection or mixing of oxygen into the tertiary air and quaternary, if used, should be avoided in an aerodynamically staged burner without OFA. In theory the optimization of local stoichiometric condition can be done with any oxidants including air. However, oxygen is more effective because only a small volume is required and local stoichiometric condition can be changed without a large impact on the overall aerodynamic mixing conditions of the flame.

Another important requirement is that oxygen enrichment has to be done in such a way as to preserve or enhance the physical size of the fuel rich zone (the "$N_2$ forming zone") of an aerodynamically staged flame. The method of oxygen injection and the consequent reduction of air flows in certain air passages of a burner would influence the aerodynamic staging conditions of the burner, and hence the physical size and the local stoichiometric conditions. If the size of the fuel rich zone is reduced and the average gas residence time in the fuel rich zone is reduced as a result of oxygen injection, such a change could cause NOx increases. For example, high velocity injection of oxygen through an axial lance such as the one shown in FIG. 3a would effectively increase the axial momentum of the surrounding coal/air stream, which in turn may enhance the mixing with secondary and tertiary air. As a result the size of the fuel rich NOx reduction zone of the flame may be reduced and NOx may increase. On the other hand when the oxygen flow is injected radially from an axially located oxygen lance such as the one shown in FIG. 3b near the tip of the burner, it may effectively increase the recirculation zone near the burner and hence increase the size of the fuel rich zone and further promote NOx reduction by oxygen enrichment. Complex impacts of oxygen injection on the burner aerodynamic conditions have to be evaluated carefully for a specific burner to achieve NOx reduction.

Without intending to be bound by any particular explanation of the unexpected performance of this invention, the performance of the combustion device operated in accordance with this invention is consistent with a mechanism in which the injected oxygen causes an increase in the temperature of that portion of the flame closest to the burner, which in turn causes relatively volatile components present in the hydrocarbon fuel to enter the gas phase from the fuel and undergo partial reaction with the ambient oxygen, thereby creating a relatively reducing atmosphere that enables nitrogen-containing species released from the combusting fuel to be converted to molecular nitrogen, that is, $N_2$, rather that converted to NOx compounds.

Typically, the temperature of the fuel-rich zone into which the fuel and the oxygen enter is on the order of 2500° F. or higher. Feeding the oxygen in this manner can cause the base of flame 6 to draw nearer to the opening of burner 3, or even to become attached to burner 3. However, feeding the oxygen in the manner described herein into the hydrocarbon fuel as it emerges from the burner proceeds in the same manner, even if the flame becomes attached to the burner. In steady state operation, for instance after a combustion device has been retrofitted in accordance with the teachings herein, operation of the combustion device continues on the basis that less than 25%, preferably less than 15%, of the stoichiometric amount of oxygen required for the complete combustion of the fuel is fed into the fuel, while combustion air is fed through the burner in an amount less than otherwise would be the case, so that the total amount of oxygen fed into the device is at least the stoichiometric amount needed for complete combustion of the fuel.

Although the invention has been described with reference to FIGS. 1, 2 and 3 for a wall fired boiler with multiple burners, it is also applicable to other type of boilers, including, but not limited to, tangentially fired boilers and cyclone fired boilers.

In the present invention a small amount of oxygen is used, as described above, in conjunction with switching at least some, or all, of the fuel to a lower rank (lower energy content per unit mass) fuel to reduce pollution emissions, in a manner which eliminates the needs for costly boiler modifications. It is well known that emissions of NOx, SOx and other emissions from coal fired utility boilers are strongly dependent on the type of coal fired. Thus, switching to a less polluting coal, e.g., from an Eastern bituminous coal to a Western sub-bituminous coal, preferably in combination with aforementioned methods of oxygen injection, provides synergistic reduction of emissions from coal fired boilers and furnaces. Western sub-bituminous coals and lignites typically have much lower sulfur contents and lower nitrogen contents than Eastern bituminous coals. Furthermore, sub-bituminous coals and lignites are more reactive than bituminous coals and produce lower unburned carbon (UBC) in ash. Emissions of SOx and NOx and UBC in ash can be substantially reduced by switching to less polluting coals.

A preferred embodiment is to switch some or all of the feed from bituminous coal to sub-bituminous coal or lignite. When a portion of the combustion air is replaced by oxygen, the flame temperature is increased and the flue gas volume is reduced because the reduced flow rate of air reduces the amount of nitrogen flowing through the combustion chamber. The oxygen addition effectively offsets the reduction in flame temperature and increased flue gas volume caused by switching the feed coal to a lower rank coal and restores the heat transfer conditions in the boiler. Furthermore, oxygen addition can be conducted under staged combustion conditions so as to enhance NOx reduction kinetics in the fuel rich combustion stage, as described herein.

The invention is described in detail using the following example of coal switching simulated by a computer model of boiler combustion and heat transfer.

EXAMPLE 1

A 220 MW, based on thermal input, tangentially fired boiler is fired with a bituminous coal from Pittsburgh #8 (Pit #8) coal seam as the baseline (Case 1). The feed coal is switched to a lower rank sub-bituminous coal from Powder River Basin (PRB) in Wyoming. The coal properties are summarized in Table 1.

TABLE 1

|  | Pit #8 | PRB |
|---|---|---|
| Proximate Analysis (%, wet) | | |
| moisture | 5.2 | 28.7 |
| V.M | 38.1 | 32.0 |
| F.C | 48.1 | 33.7 |
| Ash | 8.6 | 5.6 |
| Total | 100 | 100 |
| Ultimate Anaysis (%, dry) | | |
| C | 74.0 | 68.30 |
| H | 5.1 | 4.91 |

TABLE 1-continued

|  | Pit #8 | PRB |
|---|---|---|
| N | 1.6 | 1.00 |
| O | 7.9 | 17.25 |
| S | 2.3 | 0.70 |
| ASH | 9.1 | 7.84 |
| Total | 100 | 100 |
| HHV (btu/lb, wet) | 12540 | 8650 |

In Table 2, operating characteristics of the boiler are summarized for the following six cases.

Case 1. Baseline operation with Bituminous coal (Pit #8) with air
Case 2. Operation with Sub-bituminous coal (PRB) with air at same fuel input
Case 3. Operation with Sub-bituminous coal (PRB) with air at increased fuel input
Case 4 Operation with Sub-bituminous coal (PRB) with oxygen enriched air at same fuel input
Case 5 Operation with Sub-bituminous coal (PRB) with oxygen enriched air at increased fuel input
Case 6 Operation with Sub-bituminous coal (PRB) with oxygen enriched air at increased fuel input, in-line duct burner turned off In the baseline operation, Case 1, 60,372 lb/hr of bituminous coal was fired with 9,144,000 SCFH of combustion air. The total heat input corresponds to 756.6 MMBtu/hr based on higher heating value (HHV) and the overall stoichiometric ratio was set at 1.18 to the provide 3% excess O2 in the flue gas. 50% of the moisture in the coal was vaporized in the pulverizer and the transport line to the burner. About 20% of stoichiometric combustion air was used to transport the pulverized coal as primary air and the temperature was 153 F. The balance of the air was used as secondary air for combustion and preheated to 522° F. in the air heater. No over fire air ports were used to stage the combustion. In the radiant furnace section, 342.5 MMBtu/hr of heat was absorbed to the boiler waterwalls, generating steam. Furnace exist gas temperature (FEGT) was 2144 F. 71.6 and 85.2 MMbtu/hr of heat was transferred to the finishing superheater section and the reheater section respectively and the flue gas temperature was reduced to 1520° F. Then, flue gas passed through the primary superheater/economizer section and the air heater and was exhausted from a stack. The boiler efficiency was 83.5% based on HHV of the fuel input.

TABLE 2

| | Boiler Operations | | | | | |
|---|---|---|---|---|---|---|
| | Case 1 | Case 2 | Case 3 | Case 4 | Case 5 | Case 6 |
| Case Definition: | | | | | | |
| Coal type | Pit. #8 | PRB | PRB | PRB | PRB | PRB |
| % of moisture vaporized in mill | 50 | 50 | 50 | 50 | 50 | 6 |
| In-duct burner (Y/N) | N | Y | Y | Y | Y | N |
| O2% in oxidant | 20.67 | 20.67 | 20.67 | 22.26 | 22.02 | 22.02 |
| Furnace Operation: | | | | | | |
| Coal flow (lb/hr) | 60372 | 87522 | 92160 | 87522 | 90147 | 91367 |
| Firing rate (MMBtu/hr, HHV) | 756.6 | 756.6 | 796.7 | 756.6 | 779.3 | 789.8 |

TABLE 2-continued

| | Boiler Operations | | | | | |
|---|---|---|---|---|---|---|
| | Case 1 | Case 2 | Case 3 | Case 4 | Case 5 | Case 6 |
| In-duct burner(MMBtu/hr,HHV) | 0 | 13.2 | 13.2 | 13.2 | 13.2 | 0 |
| Oxidant flow (SCFH) | 9144000 | 9054000 | 9532800 | 8312400 | 8668800 | 8643600 |
| Flue Gas Temperatures (F.): | | | | | | |
| Furnace exit (FEGT) | 2144 | 2092 | 2122 | 2102 | 2122 | 2115 |
| Leaving reheater | 1520 | 1506 | 1536 | 1491 | 1514 | 1511 |
| Leaving economizer | 850 | 851 | 895 | 821 | 854 | 850 |
| Heat Absorptions (MMBtu/hr): | | | | | | |
| Waterwalls | 342.5 | 320.3 | 329.4 | 341.9 | 342.9 | 342.9 |
| Finishing Superheater | 71.6 | 70.0 | 73.1 | 69.2 | 72.2 | 71.7 |
| Reheater | 85.2 | 84.0 | 89.9 | 81.7 | 85.0 | 84.4 |
| Primary Superheater + Economizer | 132.2 | 136.3 | 140.6 | 130.0 | 133.3 | 133.1 |
| Total | 631.5 | 610.6 | 633.0 | 622.8 | 633.4 | 632.1 |
| Boiler Efficiency: | | | | | | |
| Gross (% of HHV coal input) | 83.5 | 80.7 | 79.5 | 82.3 | 81.3 | 80.0 |
| Net (% of HHV coal + NG input) | 83.5 | 79.3 | 78.2 | 80.9 | 79.9 | 80.0 |

In Cases 2 to 6, coal was switched to the sub-bituminous PRB coal. In Case 2, 87,522 lb/hr of sub-bituminous coal was fired with 9,054,000 SCFH of combustion air to maintain the same total heat input of 756.6 MMBtu/hr as the baseline. The overall stoichiometric ratio was adjusted at 1.19 to provide 3% excess O2 in the flue gas. About 20% of stoichiometric combustion air was used to transport the pulverized coal as primary air and the temperature was maintained at 153 F. In order to vaporize about 50% of the moisture contained in the as received coal in the coal pulverizer and the transport lines, in-duct burners were used and 13.2 MMBtu/hr of natural gas was consumed. The balance of the air was used as secondary air for combustion and preheated to 522° F. in the air heater. No other changes were made to the boiler operation. In the radiant furnace section, 320.3 MMBtu/hr of heat was absorbed to the boiler waterwalls, generating steam. Furnace exist gas temperature (FEGT) was reduced to 2,092° F. and 70.0 and 84.0 MMBtu/hr of heat was transferred to the finishing superheater section and the reheater section respectively and the flue gas temperature was reduced to 1506° F. Although the same heat input was maintained, Heat aborption by water walls, superheater and reheater sections were reduced by 6.5%, 2.2%, and 1.4% respectively, caused by the reduced flame temperature. On the other hand heat fluxes to the primary superheater/economizer section increased due to the greater flue gas volume and higher flue gas velocity. In this case the total heat absorption and hence the steam production was reduced by 3.3% as compared with the baseline case fired with the bituminous coal. The flue gas volume was increased by 5.04% with a corresponding increase in the flue gas velocity. The boiler efficiency was reduced by 2.8% to 80.7% based on HHV of the coal input. The net boiler efficiency including the HHV of the natural gas used to dry the coal was 79.3%, which represents 4.2% reduction as compared with the baseline case with bituminous coal.

In order to overcome the shortfall in steam output in Case 2, the fuel input was increased to 796.7 MMBtu/hr in Case 3, while maintaining other combustion parameters such as stoichiometric ratio and air preheat temperature. The total boiler heat absorption was 633.0 MMBtu/hr, which closely matched the baseline condition. Furnace exist gas temperature (FEGT) was increased to 2122° F. and 73.1 and 89.9 MMBtu/hr of heat was transferred to the super heater section and the reheater section respectively and the flue gas temperature was increased to 1536° F. Although the same total heat absorption was achieved as compared to the baseline Case 1, substantial increases in heat absorption to superheater and reheater sections resulted. Although the steam temperature increase caused by the higher superheater and reheater heat absorption were controlled by feed water injection in the attemperator in this boiler, the high temperature limitation at the superheater may cause a capacity limitation in some other boilers. A significant efficiency loss was observed due to higher gas temperature after the economizer. The boiler efficiency was reduced by 4.0% to 79.5% based on HHV of the coal input. The net boiler efficiency including the HHV of the natural gas used to dry the coal was 78.2%, which represents 5.3% reduction as compared with the baseline case with bituminous coal.

In Case 4, oxygen enrichment of air was used to increase the the heat absorption at waterwalls while maintaining the same fuel input and other combustion parameters in Case 1 except the fuel type. By enriching the oxygen concentration of the combustion air to 22.26%, 341.9 MMBtu/hr of heat was absorbed by the boiler waterwalls, which closely matched the baseline condition. Furnace exist gas temperature (FEGT) was 2102° F. and 69.2 and 81.7 MMBtu/hr of heat was transferred to the superheater section and the reheater section respectively and the flue gas temperature was reduced to 1491° F. A significant efficiency gain, compared to Case 2, was observed due to lower gas temperature after the economizer. Although the same total heat absorption was achieved in the waterwalls as compared to the baseline Case 1, heat absorptions to the finishing superheater, the reheater and the primary superheater/economizer sections were substantially decreased due to the smaller flue gas volume. The boiler efficiency was decreased by 1.2% to 82.3% based on HHV of the coal input. The net boiler efficiency including the HHV of the natural gas used to dry the coal was 80.9%, which represents 2.6% reduction as compared with the baseline case with bituminous coal.

In Case 5, fuel input was increase in combination with oxygen enrichment of air to match the heat transfer conditions of baseline Case 1. By increasing the fuel input to 779.3 MMBtu/hr and enriching the oxygen concentration of the combustion air to 22.02%, all heat fluxes are closely matched to those of Case 1. This example shows that it is possible to restore the original heat transfer conditions of bituminous coal and air combustion by switching fuel to sub-bituminous coal and enriching air with oxygen.

In Case 6, the natural gas fired in-duct burners were turned off and fuel input was increased in combination with oxygen enrichment of air to match the heat transfer conditions of baseline Case 1. By increasing the fuel input to 789.8 MMBtu/hr and enriching the oxygen concentration of the combustion air to 22.02%, individual and total heat fluxes to the boiler heat transfer surfaces are closely matched to those of Case 1 without requiring the in-duct burners. There is a significant economic benefits in eliminating the needs for in-duct burner fired by natural gas which is a more expensive fuel than coal.

Although the foregoing examples illustrate the invention based on switching the type of coal from bituminous to sub-bituminous coal, the invention is applicable to general fuel switching from a fuel or mixture of fuels with a given adiabatic flame temperature to another fuel or mixture of fuels containing at least a fuel which is different from the original fuels which possesses a lower adiabatic flame temperature and a greater flue gas volume For example, co-firing of biomass such as sludge, animal wastes in a coal fired boiler by partially replacing coal with biomass would be considered as part of the present invention In general, oxygen enrichment increases the flame temperature and the available heat at high temperatures. Since the boiler furnace exit gas temperature is typically in a range between 2000 F. and 2400 F., the available heat of combustion for a fuel with air under stoichiometric condition would be the best parameter to compare different fuels and the amount of oxygen required, although higher flame temperature always correlates with higher available heat. The heat flux to boiler waterwalls is closely coupled with the available heat above 2000 F., although the heat transfer properties such as flame and gas emissivities have secondary impacts on heat absorption by waterwalls.

What is claimed is:

1. A method for modifying operation of a furnace, comprising to a furnace that comprises a combustion chamber, burner means for combusting hydrocarbonaceous fuel containing bound nitrogen and having a given minimum calorific value in said combustion chamber to generate heat of combustion and gaseous combustion products, feed means for feeding said fuel and combustion air to said burner means, flue means for enabling said combustion products to leave said combustion chamber, and heating means for using said heat of combustion to produce steam, wherein said furnace is being operated to combust a first fuel containing bound nitrogen and having said minimum calorific value to produce steam at a defined minimum rate of energy content per unit of time, providing replacement fuel by replacing some or all of said first fuel with a second hydrocarbonaceous fuel whose calorific value is below that of the first fuel, at a replacement ratio such that the feed rate of said second fuel to said furnace divided by the feed rate of said first fuel to said furnace in units of energy per unit time is between 1.0 to 1.3, and feeding said replacement fuel to said burner means, feeding gaseous oxygen into said replacement fuel as the replacement fuel emerges from said burner into said combustion chamber or by adding it to air that is fed through said burner, in an amount which is less than 25% of the stoichiometric amount required for complete combustion of said replacement fuel while reducing the amount of air fed through said burner by an amount containing sufficient oxygen that the overall stoichiometric ratio in said furnace varies by not more than 10% compared to the stoichiometric ratio without said addition of oxygen, and combusting said replacement fuel with said combustion air and said oxygen.

2. The method of claim 1 wherein the calorific values of said first fuel and said second fuel are related such that the available heat above 2000 F. generated by combusting said first fuel with air at a given stoichiometric ratio and temperature is 103% or more of the available heat above 2000 F. generated by combusting said second fuel with air at said given stoichiometric ratio and temperature.

3. The method of claim 1 wherein said oxygen is fed to said burner at a sufficient rate that said furnace produces steam at a rate of energy content per unit of time at least equal to said defined minimum rate.

4. The method of claim 1 wherein said first fuel is bituminous coal and said second fuel optionally comprises bituminous coal and further comprises coal selected from the group consisting of subbituminous coal, lignite and mixtures thereof.

5. The method of claim 1 wherein said combustion is staged with over fire air and the primary combustion zone stoichiometric ratio is between 0.6 and 1.0.

6. A method according to claim 1 wherein a stream of fuel is fed through said burner and oxygen is fed into said fuel by injecting it through a hollow lance, positioned in said stream, into the fuel as the fuel emerges from the burner.

7. A method according to claim 1 wherein a stream of fuel is fed through an annular fuel passage of said burner, and oxygen is fed into said fuel by injecting it through an annular passage surrounding or surrounded by said annular fuel passage.

* * * * *